United States Patent
Rippe et al.

(10) Patent No.: US 10,856,924 B2
(45) Date of Patent: Dec. 8, 2020

(54) HEADLESS COMPRESSION SCREW DRIVER SYSTEM

(71) Applicant: GLOBUS MEDICAL, INC., Audubon, PA (US)

(72) Inventors: Bradford H. Rippe, Conshohocken, PA (US); Peter Govey, Philadelphia, PA (US); James Gault, Philadelphia, PA (US); Andrew Davison, Downingtown, PA (US)

(73) Assignee: Globus Medical Inc., Audubon, PA (US)

( * ) Notice: Subject to any disclaimer, the term of this patent is extended or adjusted under 35 U.S.C. 154(b) by 265 days.

(21) Appl. No.: 15/849,774

(22) Filed: Dec. 21, 2017

(65) Prior Publication Data

US 2019/0192206 A1 Jun. 27, 2019

(51) Int. Cl.
| | |
|---|---|
| *A61B 17/88* | (2006.01) |
| *B25B 23/10* | (2006.01) |
| *B25B 23/00* | (2006.01) |
| *A61B 17/00* | (2006.01) |
| *A61B 90/00* | (2016.01) |
| *A61B 17/56* | (2006.01) |

(Continued)

(52) U.S. Cl.
CPC ...... *A61B 17/8875* (2013.01); *A61B 17/8891* (2013.01); *B25B 23/0035* (2013.01); *B25B 23/101* (2013.01); *B25B 23/103* (2013.01); *A61B 17/863* (2013.01); *A61B 17/8645* (2013.01); *A61B 2017/00477* (2013.01); *A61B 2017/564* (2013.01); *A61B 2017/681* (2013.01); *A61B 2090/035* (2016.02)

(58) Field of Classification Search
CPC .............. A61B 17/8875; A61B 17/888; B25B 23/1405; B25B 23/1142
See application file for complete search history.

(56) References Cited

U.S. PATENT DOCUMENTS

| | | |
|---|---|---|
| 3,651,718 A | 3/1972 | Thomasian |
| 5,431,660 A * | 7/1995 | Burke ................ A61B 17/8685 411/1 |

(Continued)

FOREIGN PATENT DOCUMENTS

| | | |
|---|---|---|
| EP | 2918238 A1 | 9/2015 |
| EP | 3235458 A1 | 10/2017 |
| WO | 2012/141715 A1 | 10/2012 |

*Primary Examiner* — Nicholas W Woodall

(57) ABSTRACT

A compression screw driver system including a drive member having a shaft extending from a proximal end to a distal end. A drive selection member is positioned about the shaft and is axially moveable along the shaft between an engagement position and a disengaged position. A distal portion of the drive selection member defines a first engagement structure. A compression sleeve is positioned over the distal end of the shaft. The proximal end of the compression sleeve defines a second engagement structure which complements the first engagement structure and the distal end of the compression sleeve defines a contact surface. In the engagement position the first and second engagement structures are engaged and the compression sleeve rotates with the drive member and in the disengaged position the first and second engagement structures are disengaged and the compression sleeve remains stationary while the drive member rotates.

17 Claims, 7 Drawing Sheets

(51) Int. Cl.
*A61B 17/86* (2006.01)
*A61B 17/68* (2006.01)

(56) References Cited

U.S. PATENT DOCUMENTS

| | | | |
|---|---|---|---|
| 7,272,999 B2 * | 9/2007 | Cutler | B25B 15/02 |
| | | | 81/467 |
| 7,334,509 B1 * | 2/2008 | Gao | B25B 15/02 |
| | | | 81/467 |
| 7,762,164 B2 | 7/2010 | Nino et al. | |
| 7,938,046 B2 | 5/2011 | Nino et al. | |
| 8,216,243 B2 | 7/2012 | Yevmenenko et al. | |
| 8,540,726 B2 | 9/2013 | Yevmenenko et al. | |
| 9,113,976 B2 | 8/2015 | Yevmenenko et al. | |
| 9,161,793 B2 | 10/2015 | Huebner | |
| 9,241,751 B2 * | 1/2016 | Nino | B25B 13/466 |
| 9,259,258 B2 | 2/2016 | Laurenti | |
| 9,409,285 B2 * | 8/2016 | Ivinson | B25B 23/1422 |
| 9,498,229 B2 | 11/2016 | Harris, Jr. et al. | |
| 10,160,105 B2 * | 12/2018 | Nino | A61B 17/8875 |
| 2006/0016300 A1 * | 1/2006 | Bubel | B25B 23/1427 |
| | | | 81/475 |
| 2010/0211115 A1 | 8/2010 | Tyber et al. | |
| 2012/0055296 A1 * | 3/2012 | Landowski | F16D 7/08 |
| | | | 81/474 |
| 2016/0038203 A1 | 2/2016 | Huebner | |
| 2016/0354132 A1 * | 12/2016 | Nino | A61B 17/8875 |
| 2017/0035485 A1 * | 2/2017 | Ivinson | B25B 23/141 |

* cited by examiner

HEADLESS COMPRESSION SCREW DRIVER SYSTEM

FIELD

The present disclosure relates to headless compression screws. More particularly, the disclosure relates to headless compression screw driver systems and methods for implanting headless compression screws.

BACKGROUND

One method of reducing a fracture across two bone fragments is driving a compression screw across the fracture site. Some compression screws can have a variable thread pitch along the length of the screw to aid in compressing the fracture while other compression screws allow the head to rotate independently from the distal threads. For fractures in areas of minimal soft tissue coverage or near articular surfaces, it can be desirable to have a compression screw with no head, such that the screw can be countersunk into the bone. With such screws, an insertion tool may be used to generate compression by means of a more traditional lag technique.

While headless screws on the market have proven their merits clinically, the need for improvement on instrumentation, ease of use and generated compression has been documented in a number of papers. In more than one study, a loss of generated compression has been measured and documented with some instruments when transitioning from screw insertion/compression to countersinking. This is likely due to the need for the removal of the insertion handle and insertion of the cannulated driver during a critical point in the insertion.

SUMMARY

In at least one embodiment, the present disclosure provides a driver mechanism that allows a headless compression screw to be inserted and countersunk, without needing to change out instrumentation. The device should allow improved ease-of-use for the surgeon and potentially greater interfragmentary compression.

In at least one embodiment, the present disclosure provides a compression screw driver system including a drive member having a shaft extending from a proximal end to a distal end with a drive tip defined on the distal end. A drive selection member is positioned about the shaft and secured thereto such that the drive selection member rotates with the shaft and is axially moveable along the shaft between an engagement position and a disengaged position. A distal portion of the drive selection member defines a first engagement structure. A compression sleeve having a tubular body extending from a proximal end to a distal end with a through passage therethrough is positioned over the distal end of the shaft with threads within the through passage threadably engaging threads on the shaft. The proximal end of the compression sleeve defines a second engagement structure which complements the first engagement structure and the distal end of the compression sleeve defines a contact surface. In the engagement position the first and second engagement structures are engaged and the compression sleeve rotates with the drive member and in the disengaged position the first and second engagement structures are disengaged and the compression sleeve remains stationary while the drive member rotates.

In at least one embodiment, the present disclosure provides a method of implanting a headless compression screw into a bone through a bone contacting surface utilizing a driver system including a drive member including a shaft extending from a proximal end to a distal end with a drive tip defined on the distal end; a drive selection member positioned about the shaft and secured thereto such that the drive selection member rotates with the shaft and is axially moveable along the shaft between an engagement position and a disengaged position, a distal portion of the drive selection member defining a first engagement structure; and a compression sleeve having a tubular body extending from a proximal end to a distal end with a through passage therethrough is positioned over the distal end of the shaft with threads within the though passage threadably engaging threads on the shaft, the proximal end of the compression sleeve defines a second engagement structure which complements the first engagement structure and the distal end of the compression sleeve defines a contact surface. The method includes positioning the headless compression screw on the drive tip; rotating the drive member with the drive selection member in the engagement position such that the headless compression screw is advanced into the bone and the compression sleeve is advanced until the contact surface is in contact with the bone surface; continuing to rotate the drive member with the drive selection member in the engagement position such that the headless compression screw is further advanced and the compression sleeve creates compression in the bone; moving the drive selection member to the disengaged position; rotating the drive member with the drive selection member in the disengaged position such that the headless compression screw is further advanced into the bone and the compression sleeve remains stationary while maintaining compression in the bone.

DETAILED DESCRIPTION

Figure 1:
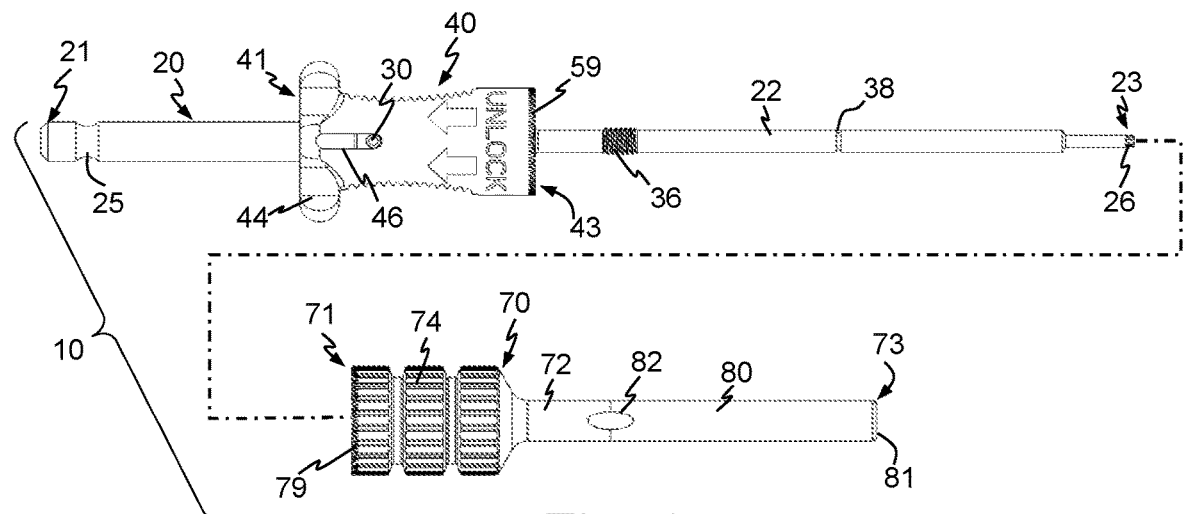
FIG. 1 is a bottom plan view of a headless compression screw driver system in accordance with an embodiment of the disclosure, with the compression sleeve disassembled from the drive member.

It is to be understood that the present disclosure is not limited in its application to the details of construction and the arrangement of components set forth in the description herein or illustrated in the drawings. The teachings of the present disclosure may be used and practiced in other embodiments and practiced or carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

The following discussion is presented to enable a person skilled in the art to make and use embodiments of the present disclosure. Various modifications to the illustrated embodiments will be readily apparent to those skilled in the art, and the principles herein can be applied to other embodiments and applications without departing from embodiments of the present disclosure. Thus, the embodiments are not intended to be limited to embodiments shown, but are to be accorded the widest scope consistent with the principles and features disclosed herein. The following detailed description is to be read with reference to the figures, in which like elements in different figures have like reference numerals. The figures, which are not necessarily to scale, depict selected embodiments and are not intended to limit the scope of the embodiments. Skilled artisans will recognize the examples provided herein have many useful alternatives and fall within the scope of the embodiments.

Figure 2:
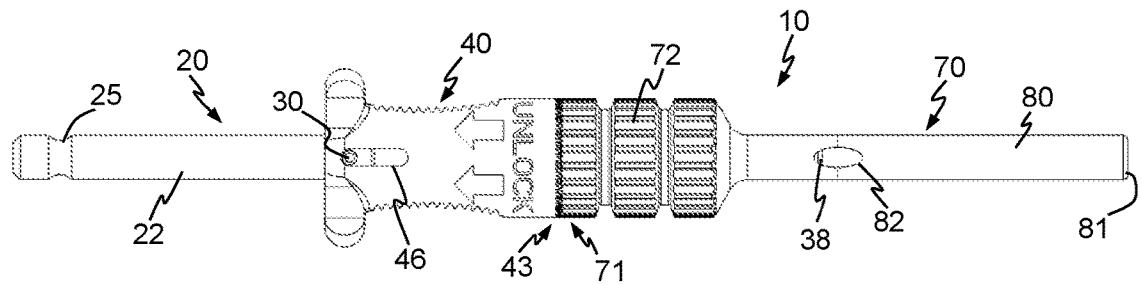
FIGS. 2, 3 and 4 are bottom, side and top views, respectively, of the headless compression screw driver system of FIG. 1 with the compression sleeve assembled on the drive member and in an engaged position.
Figure 3:
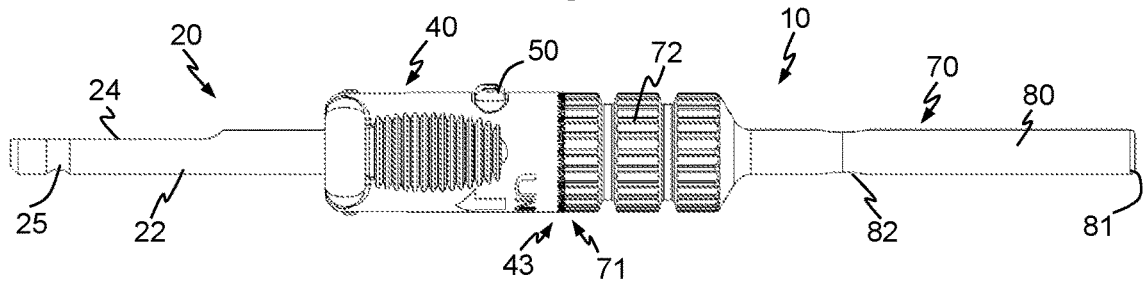
Figure 4:
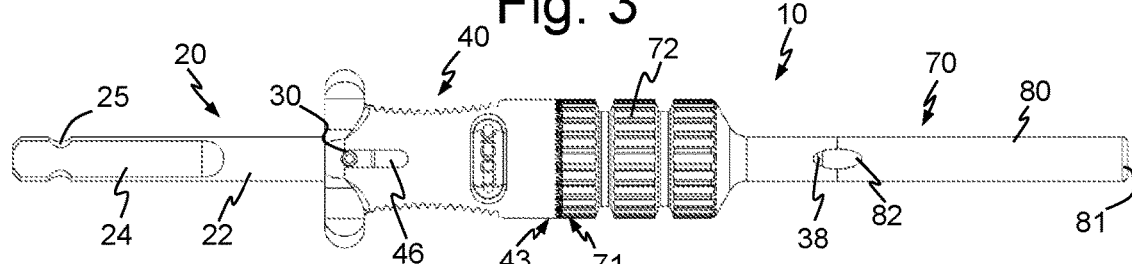
Figure 5:
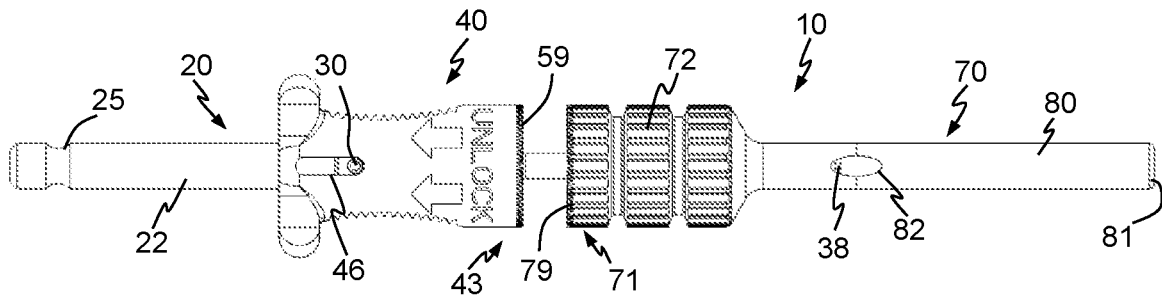
FIGS. 5, 6 and 7 are bottom, side and top views, respectively, of the headless compression screw driver system of FIG. 1 with the compression sleeve assembled on the drive member and in a disengaged position.
Figure 6:
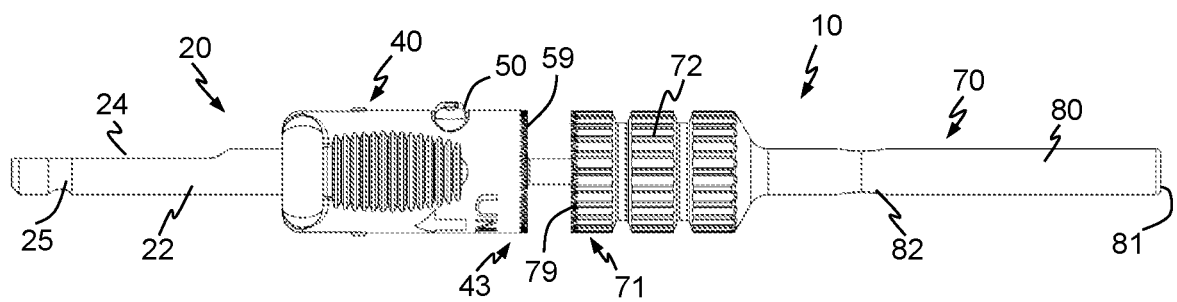
Figure 7:
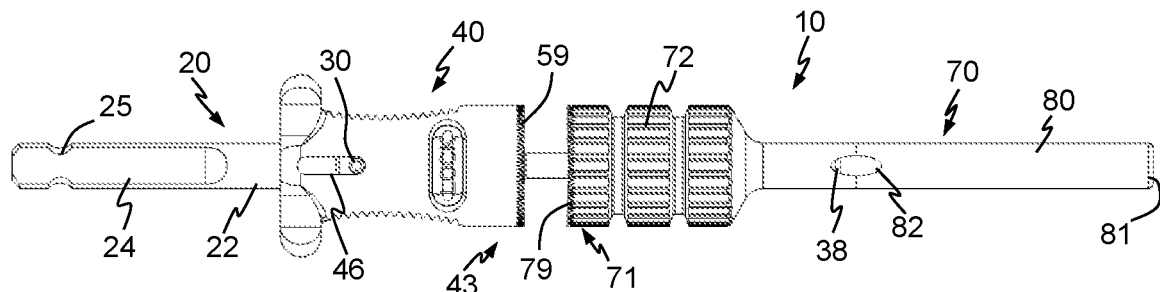
Figure 8:
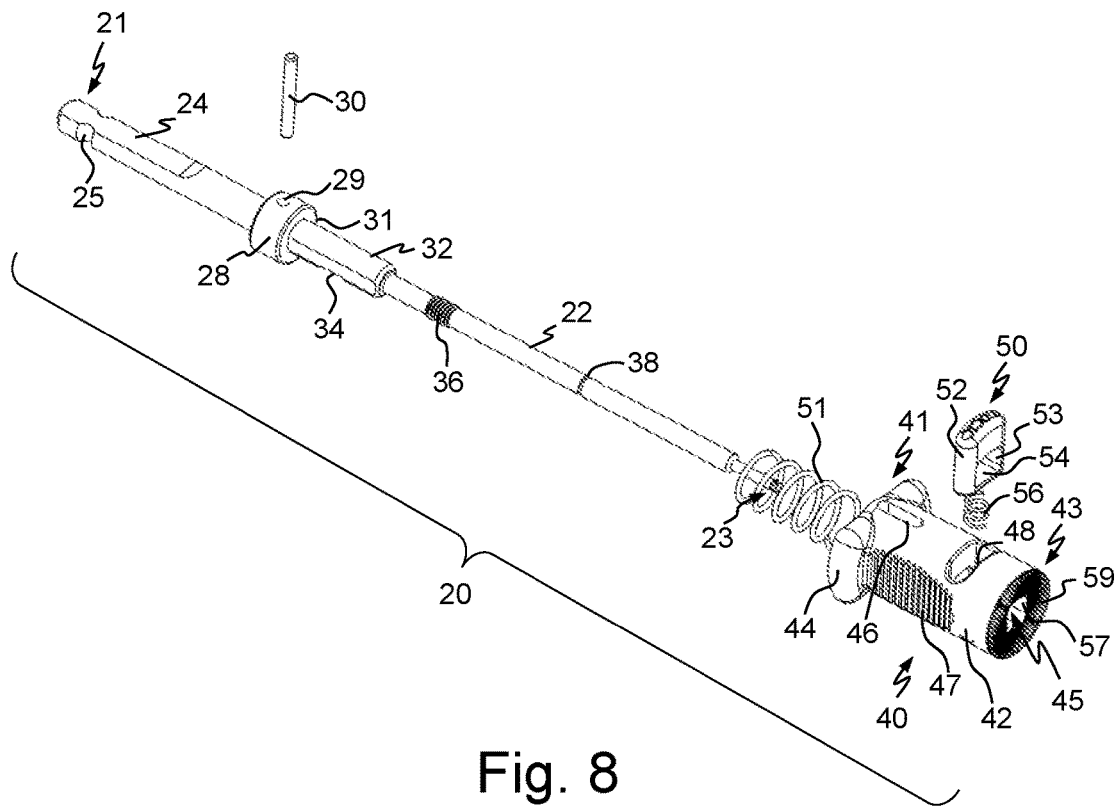
FIG. 8 is an exploded perspective view of the drive member of FIG. 1.

With reference to FIGS. 1-11, a headless compression screw driver system 10 in accordance with an embodiment of the disclosure will be described. The headless compression screw driver system 10 generally comprises a drive member 20 and a compression sleeve 70. As will be described in more detail hereinafter, the drive member 20 and the compression sleeve 70 are configured such that the may be rotated together or the drive member 20 may be rotated independently of the compression sleeve 70. More specifically, when a drive selection member 40 is engaged with the compression sleeve 70, as illustrated in FIGS. 2-4, the compression sleeve 70 rotates together with the drive member 20. This would be the position in which the surgeon would insert the headless screw and gain interfragmentary compression. When the drive selection member 40 is disengaged from the compression sleeve 70, as illustrated in FIGS. 5-7, the drive member 20 rotates independently from the compression sleeve 70. This would be the position where the surgeon could drive the screw out of the compression sleeve 70 and into the near-cortex to countersink. Headless compression screw driver 10 may also have a cannulated configuration such that driver 10 is configured to be disposed over a K-wire.

Referring to FIGS. 1 and 8-11, the drive member 20 includes a shaft 22 extending from a proximal end 21 to a distal end 23. The proximal end 21 is configured to engage a handle or the like (not shown). For example, the illustrated embodiment includes a flat area 24 and a groove 25. The distal end 23 of the shaft 22 includes a screw engaging tip 26, for example, a hexalobular drive tip, however, other configurations may be utilized. Since the shaft 22 is continuous, application of a rotation force to the proximal end 21, via a handle or the like, causes direct rotation of the screw engaging tip 26 and thereby a screw 100 positioned thereon (see FIG. 12).

A radial flange 28 extends from an intermediate portion of the shaft 22. In the illustrated embodiment, the flange 28 is formed integral with the shaft 22, but may alternatively be formed separately and attached thereto. A transverse bore 29 extends through the flange 28 and shaft 22 and is configured to receive a connecting pin 30. As described in more detail below, the connecting pin 30 extends through slots 46 in the drive selection member 40 and through the bore 29 to fix the drive selection member 40 on the shaft 22, with the drive selection member 40 axially moveable relative to the shaft 22. The distal surface 31 of the flange 28 defines a spring stop surface.

Figure 10:
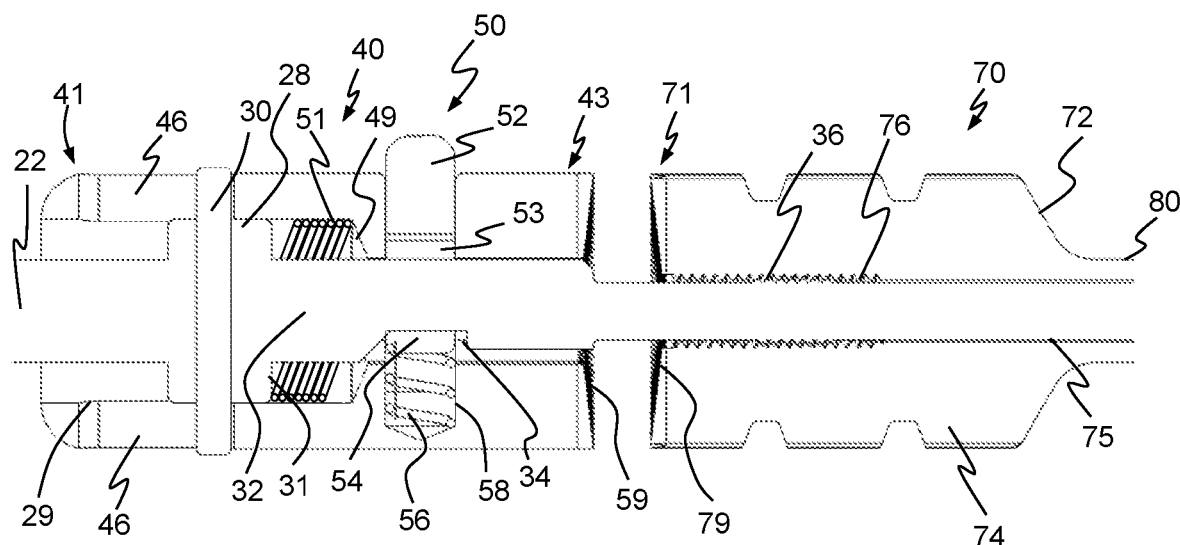
FIG. 10 is a cross-sectional view of the headless compression screw driver system.
Figure 11:
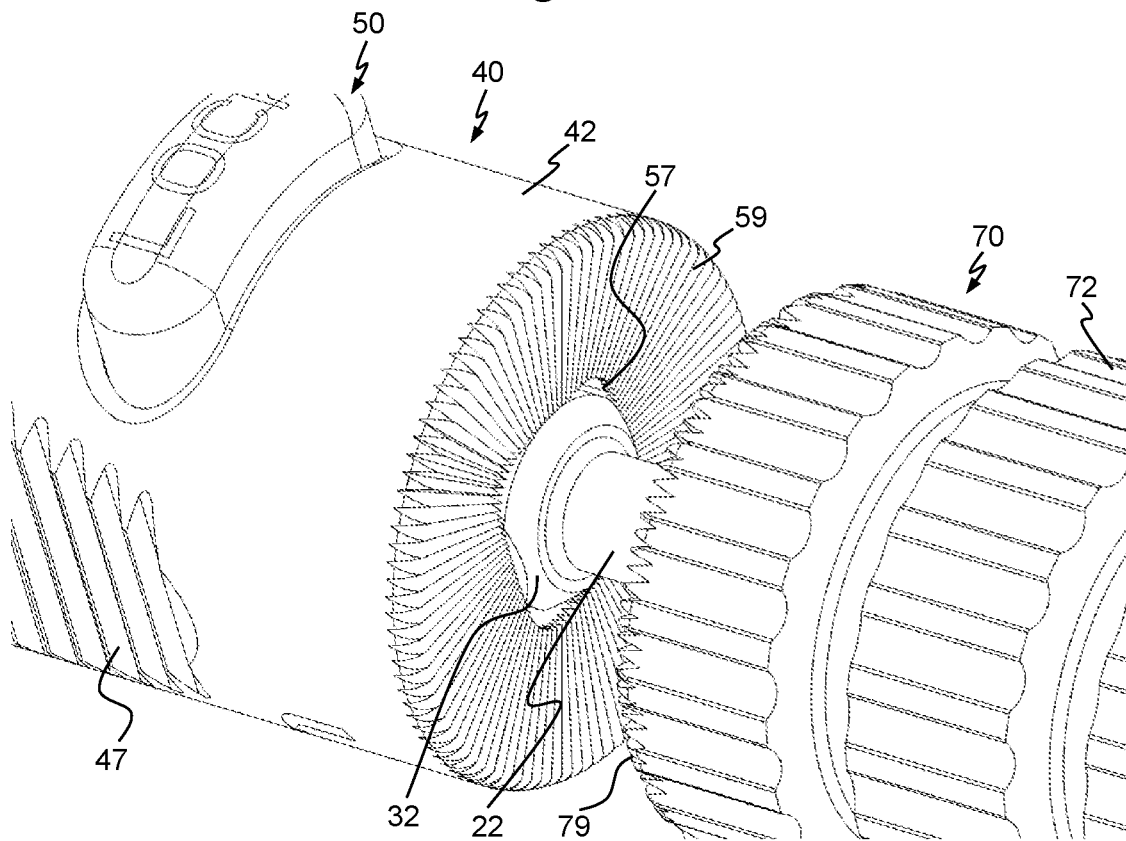
FIG. 11 is an expanded perspective view of a portion of the headless compression screw driver system with the compression sleeve in a disengaged position.

A guide portion 32 is defined along the shaft distally of the flange 28. The guide portion 32 has a configuration which complements a distal portion 57 of the passage 45 extending through the drive selection member 40, as shown in FIG. 11. With such a matching configuration, the drive selection member 40 rotates in conjunction with rotation of the shaft 22. In the illustrated embodiment, the guide portion 32 has a squared cylindrical configuration, however, other configurations may be utilized. A notch 34 is defined in the guide portion 32 and is configured to receive a portion 54 of a lock button 50, as will be described hereinafter, to lock the drive selection member 40 in the disengaged position, as illustrated in FIG. 10. Distally of the guide portion 32, the shaft 22 defines a plurality of threads 36 configured to engage internal threads 76 of the compression sleeve 70 such that the compression sleeve 70 is threadably supported relative to the shaft 22. Additionally, the shaft 22 may include a groove 38, markings or the like which may be utilized to indicate position or depth of the drive member 20 relative to the compression sleeve 70, as will be described in more detail hereinafter.

The drive selection member 40 includes a tubular body 42 extending between a proximal end 41 and a distal end 43. A through passage 45 runs through the tubular body 42 from the proximal end 41 to the distal end 43. Finger pads 44 and/or grooves 47 may be provided along the tubular body 42 to facilitate gripping of the drive selection member 40 and moving it proximally to selectively disengage the drive selection member 40 from the compression sleeve 70. The slots 46 extend through the tubular body 42 in an axial direction. As previously discussed, the connection pin 30 extends into the slots 46 to lock the drive selection member 40 onto the shaft 22, with the slots 46 defining an axial range of motion of the drive selection member 40 relative to the shaft 22. It should also be noted that more than one pair of slots 46 may be disposed in drive selection member 40. For example, more than one pair of slots 46 may be used when headless compression screw driver is configured to be cannulated.

Figure 9:
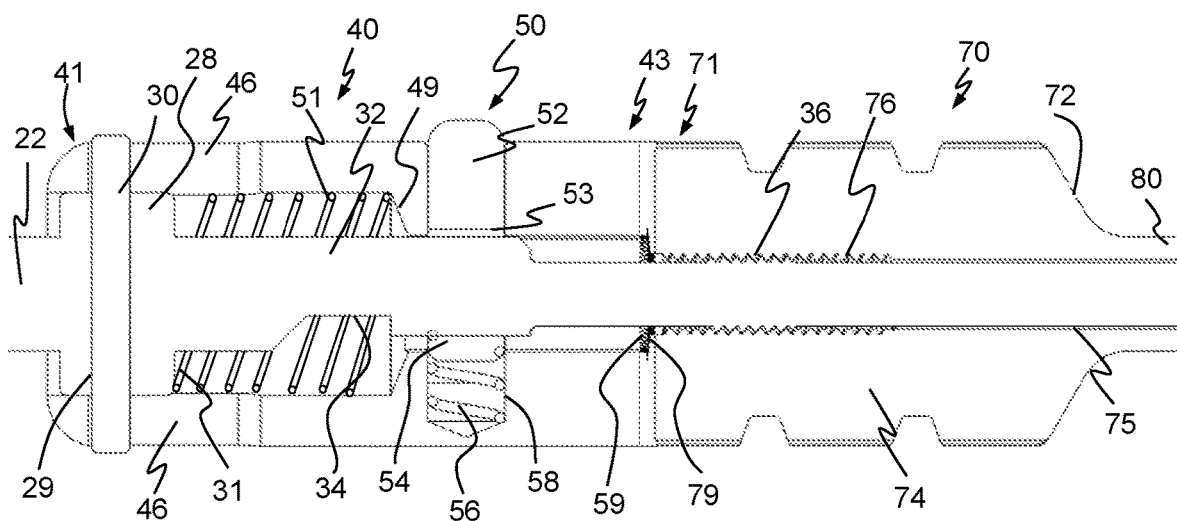
FIG. 9 is a cross-sectional view of the headless compression screw driver system.

An engagement spring 51 is positioned within the passage 45 and extends between the flange distal surface 31 and an internal shoulder 49 within the passage 45 (see FIG. 9). The engagement spring 51 is configured to bias the drive selection member 40 away from the flange 28, i.e. distally toward the engagement position as shown in FIG. 9. As seen in FIG. 11, the distal end of the tubular body 42 defines a plurality of radial teeth 59 which are configured to engage radial teeth 79 on the proximal end of the compression sleeve 70 when the drive selection member 40 is in the engagement position. With the teeth 59, 79 engaged, the compression sleeve 70 is caused to rotate in conjunction with rotation of the shaft 22. Exemplary teeth 59, 79 may be 0.5 mm, 30 degree teeth.

While radial teeth are the illustrated engagement structures, other engagement structures may be utilized, The tubular body 42 also defines a transverse bore 48 configured to receive the lock button 50. The lock button 50 has a body 52 which defines a through passage 53 which is sized and configured such that the guide portion 32 of the shaft 22 passes therethrough. A locking portion 54 of the lock button body 52 extends below the through passage 53 and is configured to engage within the notch 34 defined by the guide portion 32 when the drive selection member 40 is moved to the disengaged position, as shown in FIG. 10. A lock spring 56 is supported within a guide hole 58 within the tubular body 42. The lock spring 56 is configured to bias the lock button 50 toward the position wherein the locking portion 54 sits in the notch 34. As such, when a user pulls the drive selection member 40 proximally, against the force of the engagement spring 51, the locking portion 54 of the lock button 50 will automatically engage in the notch 34 once the drive selection member 40 is in the disengaged position. The lock button 50 will maintain the drive selection member 40 in the disengaged position until the lock button 50 is depressed, against the force of the lock spring 56, and the locking portion 54 disengages with the notch 34. Upon disengagement, the guide portion 32 of the shaft 22 is free to automatically travel under the force of the engagement spring 51 through the through passage 53 of the lock button 50 to the engagement position.

An exemplary compression sleeve 70 will be described with reference to FIGS. 1 and 9-11. The compression sleeve 70 has a tubular body 72 extending from a proximal end 71 to a distal end 73. The proximal portion 74 of the tubular body 72 has a larger diameter compared to the distal portion 80 of the tubular body 72. The larger diameter of the proximal portion 74 complements the diameter of the drive selection member 40. With such a configuration, engagement of drive selection member teeth 59 and compression sleeve teeth 79 provides a strong translation of the rotation force from the drive selection member 40 to the compression sleeve 70.

A through passage 75 extends through the tubular body 72 from the proximal end 71 to the distal end 73. The through passage 75 is sized such that the drive member shaft 22 passes therethrough. A plurality of internal threads 76 are defined along the through passage 75. In the illustrated embodiment, the threads 76 are at the proximal end of the through passage 75, however, the threads 76 may be otherwise positioned. The threads 76 are configured to threadably engage the threads 36 along the shaft 22. The threads 36, 76 are preferably the same pitch as the threads 102 of the compression screw 100. With such a configuration, the threads 36, 76 allow the screw 100 to be advanced and countersunk at the same rate that the drive member 20 moves relative to compression sleeve 70 when the drive selection member 40 is disengaged. As such, movement of the groove 38 on the shaft 22 within the window 82 defined in the distal portion of the tubular body 72 indicates the depth that the headless screw 100 has been advanced below the bone surface 111.

The distal end 73 of the tubular body 72 defines a contact surface 81 which is configured to contact the bone surface 111 (See FIG. 14) when the compression sleeve 70 is advanced with the drive member 20. Continued rotation of the drive member 20, with the drive selection member 40 in the engaged position, will cause the contact surface 81 to further press against the bone surface 111 which creates a desired compression. Once a desired compression is achieved, the drive selection member 40 is moved proximally to the disengaged position. Thereafter, the drive member 20 may be further rotated to countersink the headless screw 100.

Having generally described the components of an exemplary headless compression screw driver system 10, implantation of a headless screw 100 utilizing such a system will be described with reference to FIGS. 12-18. The headless screw 100 includes distal threads 102 and proximal countersink threads 104. The headless screw 100 includes a drive recess 106 which complements the drive member drive tip 26. The screw 100 is implanted into bone portions 110, 112 with a fracture 114 therein. The screw 100 enters the bone portion 110 at a bone surface 111.

Figure 12:
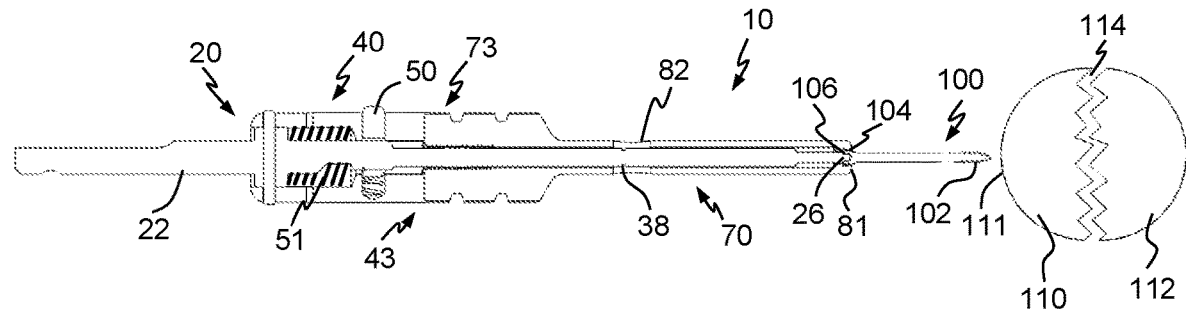
FIGS. 12-18 are cross-sectional views showing sequential implantation of a headless compression screw utilizing a headless compression screw driver system in accordance with an embodiment of the invention.
Figure 13:
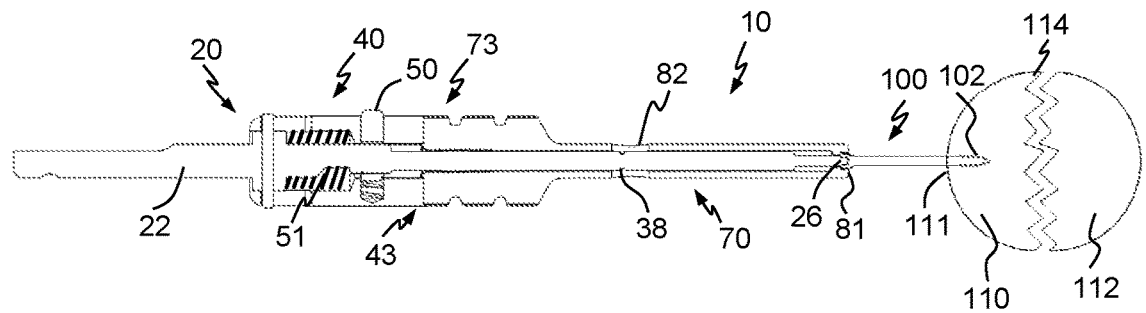
Figure 14:
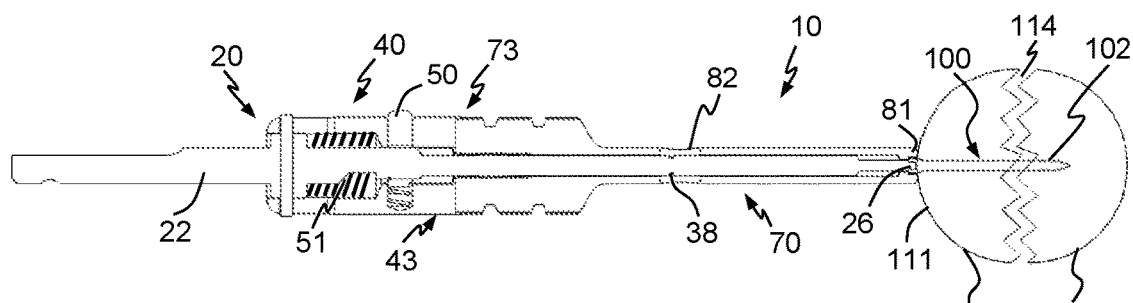
Figure 15:
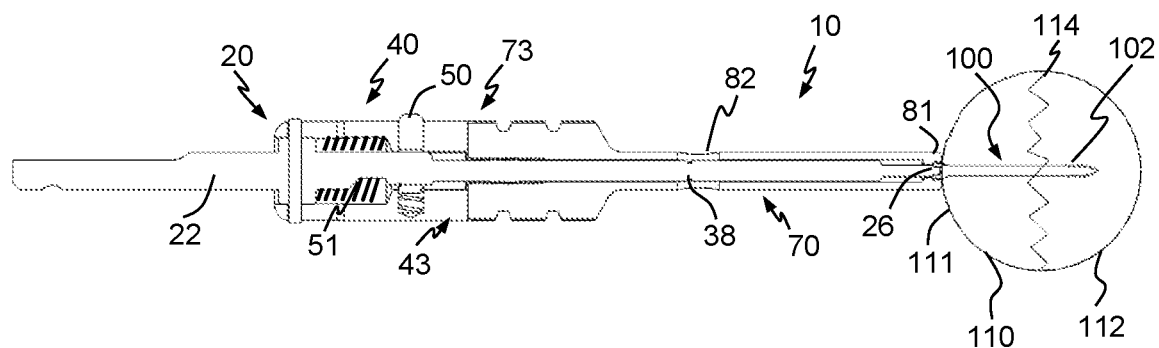

Referring to FIG. 12, the screw 100 is positioned on the screw tip 26 with the drive selection member 40 in the engaged position. Moving to FIG. 13, the drive member 20 is rotated such that the screw threads 102 are threaded through the bone surface 111 of the bone portion 110. With the drive selection member 40 engaged with the compression sleeve 70, the compression sleeve 70 rotates in conjunction with the drive member 20, maintaining the relative position of the components. Rotation of the drive member 20 continues with the screw 100 spanning the fracture 114 and entering the bone 112. Since the compression sleeve 70 advances with the drive member 20, the contact surface 81 eventually contacts the bone surface 111 as illustrated in FIG. 14. As the drive member 20 continues to be rotated, the compression sleeve 70 advances against the bone surface 111 and causes compression of the fracture 114 as shown in FIG. 15.

Figure 16:
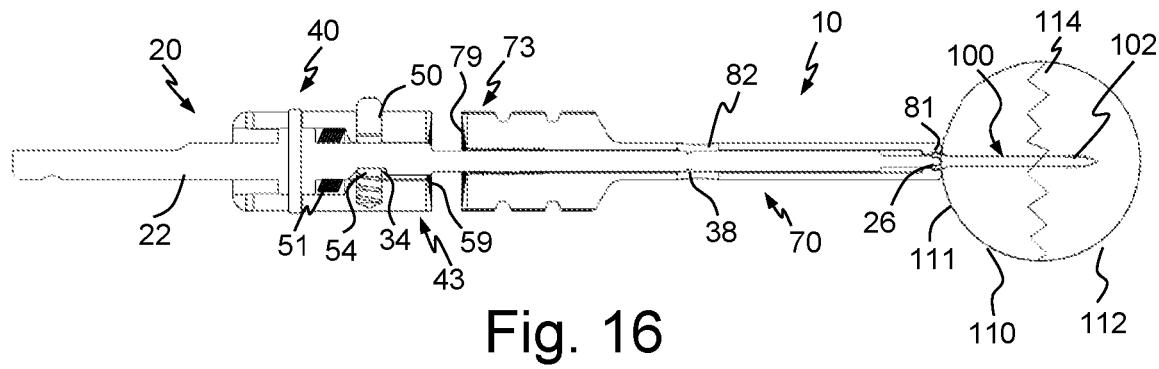
Figure 17:
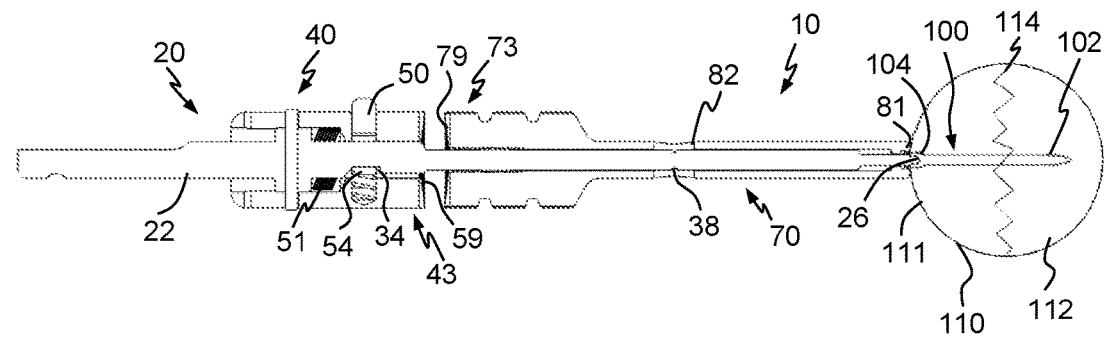
Figure 18:
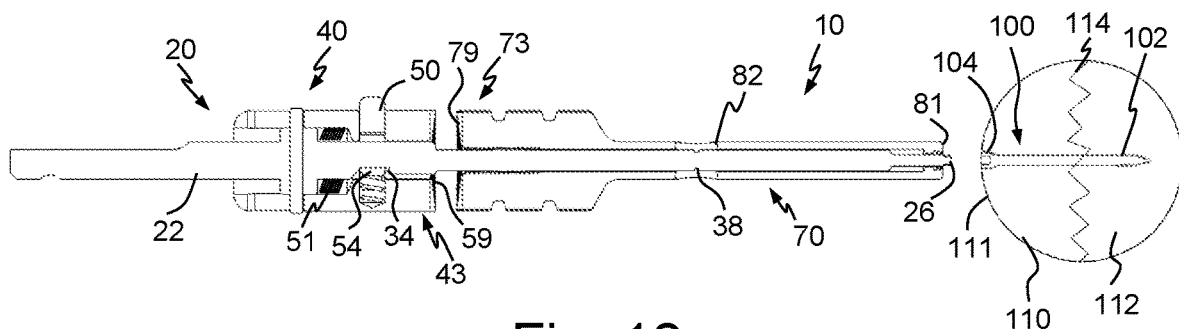

Turning to FIG. 16, once a desired compression is achieved, the drive selection member 40 is moved proximally to the disengaged position with the locking portion 54 of the lock button 50 automatically moving into the notch 34 under the force of spring 56. The lock button 50 maintains the drive selection member 40 in the disengaged position for the remainder of the procedure. As shown in FIG. 17, the drive member 20 is again rotated to further advance the screw 100, with the countersink threads 104 entering the bone portion 110. Since the compression sleeve 70 is rotationally disengaged, it does not rotate and the drive member 20 and screw 100 advance relative to the compression sleeve 70. The compression force is maintained through engagement of the threads 76 with the threads 36. The position of the groove 38 in relation to the window 82 of the compression sleeve 70 indicates to the surgeon the further depth the screw 100 has traveled. Once a desired depth has been reached, the drive tip 26 is disengaged from the screw 100 and the procedure is complete.

Although several embodiments of the disclosure have been disclosed in the foregoing specification, it is understood that many modifications and other embodiments of the disclosure will come to mind to which the invention pertains, having the benefit of the teaching presented in the foregoing description and associated drawings. It is thus understood that the systems of the disclosure are not limited to the specific embodiments disclosed hereinabove, and that many modifications and other embodiments are intended to be included within the scope of the appended claims. It is further envisioned that features from one embodiment may be combined or used with the features from a different embodiment described herein. Moreover, although specific terms are employed herein, as well as in the claims which follow, they are used only in a generic and descriptive sense, and not for the purposes of limiting the described invention, nor the claims which follow. The entire disclosure of each patent and publication cited herein is incorporated by reference, as if each such patent or publication were individually incorporated by reference herein. Various features and advantages of the invention are set forth in the following claims.

What is claimed is:

1. A compression screw driver system comprising:
   a drive member including a shaft extending from a proximal end to a distal end with a drive tip defined on the distal end;
   a drive selection member positioned about the shaft and secured thereto such that the drive selection member rotates with the shaft and is axially moveable along the shaft between an engagement position and a disengaged position, a distal portion of the drive selection member defining a first engagement structure; and
   a compression sleeve having a tubular body extending from a proximal end to a distal end with a through passage therethrough is positioned over the distal end of the shaft with threads within the though passage threadably engaging threads on the shaft, the proximal end of the compression sleeve defines a second engagement structure which complements the first engagement structure and the distal end of the compression sleeve defines a contact surface,
   wherein in the engagement position the first and second engagement structures are engaged and the compression sleeve rotates with the drive member and in the disengaged position the first and second engagement structures are disengaged and the compression sleeve remains stationary while the drive member rotates, and
   wherein the proximal end of the shaft is configured for engagement with at least one of a handle and a driving tool.

2. The system of claim 1, wherein the drive selection member includes one or more pairs of axial slots and a connection pin extends through the shaft and into the axial slots to define the axial range of motion of the drive selection member.

3. The system of claim 1, wherein a spring within the drive selection member biases the drive selection member toward the engagement position.

4. The system of claim 1, wherein a lock button extends into the drive selection member and is configured to engage a notch in the shaft when the drive selection member is in the disengaged position such that the lock button maintains the drive selection member in the disengaged position.

5. The system of claim 4, wherein the lock button is biased toward engagement with the notch.

6. The system of claim 1, wherein the first and second engagement structures are in the form of radial teeth.

7. The system of claim 1, wherein the through passage threads and the shaft threads have a pitch equal to a pitch of threads on a screw with which the system is utilized.

8. The system of claim 1, wherein the shaft has a marking thereon which aligns with a window of the compression sleeve and indicates relative movement of the drive member relative to the compression sleeve when rotated with the drive selection member in the disengaged position.

9. The system of claim 8, wherein the marking is a circumferential groove.

10. The system of claim 1, wherein the shaft includes a guide portion with a non-circular configuration which complements a non-circular portion of a through passage of the drive selection member.

11. The system of claim 1, wherein the drive selection member includes a pair of axial slots and a connection pin extends through the shaft and into the axial slots to define the axial range of motion of the drive selection member.

12. The system of claim 1, wherein a lock button extends into the drive selection member and is configured to engage a notch in the shaft when the drive selection member is in the disengaged position such that the lock button maintains the drive selection member in the disengaged position.

13. The system of claim 12, wherein the lock button is biased toward engagement with the notch.

14. The system of claim 1, wherein the shaft has a marking thereon which aligns with a window of the compression sleeve and indicates relative movement of the drive member relative to the compression sleeve when rotated with the drive selection member in the disengaged position.

15. The system of claim 14, wherein the marking is a circumferential groove.

16. The system of claim 1, wherein the shaft includes a guide portion with a non-circular configuration which complements a non-circular portion of a through passage of the drive selection member.

17. A compression screw driver system comprising:
    a drive member including a shaft extending from a proximal end to a distal end with a drive tip defined on the distal end;
    a drive selection member positioned about the shaft and secured thereto such that the drive selection member rotates with the shaft and is axially moveable along the shaft between an engagement position and a disengaged position, a distal portion of the drive selection member having a first set of radial teeth; and
    a compression sleeve having a tubular body extending from a proximal end to a distal end with a through passage therethrough is positioned over the distal end of the shaft with threads within the though passage threadably engaging threads on the shaft, the proximal end of the compression sleeve defines a second set of radial teeth which complements the first set of radial teeth and the distal end of the compression sleeve defines a contact surface,
    wherein in the engagement position the first and second sets of radial teeth are engaged and the compression sleeve rotates with the drive member and in the disengaged position the first and second sets of radial teeth are disengaged and the compression sleeve remains stationary while the drive member rotates, and
    wherein a spring within the drive selection member biases the drive selection member toward the engagement position.

\* \* \* \* \*